(12) United States Patent
Falco et al.

(10) Patent No.: US 6,573,426 B1
(45) Date of Patent: Jun. 3, 2003

(54) GENE INVOLVED IN PYRIMIDINE BIOSYNTHESIS IN PLANTS

(75) Inventors: Saverio Carl Falco, Arden, DE (US); J. Antoni Rafalski, Wilmington, DE (US); Zude Weng, Des Plains, IL (US)

(73) Assignee: E.I. du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 09/675,018

(22) Filed: Sep. 28, 2000

Related U.S. Application Data
(60) Provisional application No. 60/156,901, filed on Sep. 30, 1999.

(51) Int. Cl.[7] .......................... A01H 3/00; C07H 21/04; C07K 14/415; C12N 5/14; C12N 9/00
(52) U.S. Cl. ...................... 800/278; 435/183; 435/69.1; 435/410; 435/419; 435/252.3; 435/320.1; 530/350; 530/370; 536/23.6; 536/24.1; 536/24.33; 800/295
(58) Field of Search .............................. 435/183, 69.1, 435/410, 419, 252.3, 320.1; 530/350, 370; 536/23.6, 24.1, 24.33; 800/278, 295

(56) References Cited

PUBLICATIONS

Philip Reyes et al., Journ. of Biol. Chem., vol. 250(13):5097–5108, Jul. 10, 1975, Studies on a Pyrimidine Phosphoribosyltransferase from Murine Leukemia P1534J.
Thomas W. Traut et al., Biochemistry, vol. 19:6062–6068, 1980, Dependence of the Aggregation and Conformation States of Uridine 5'–Phosphate Synthase on Pyrimidine Nucleotides. Evidence for a Regulatory Site.
Keith Shostak et al., Biochemistry, vol. 31:12155–12161, 1992, Orotidylate Decarboxylase: Insights into the Catalytic Mechanism from Substrate Specificity Studies.
National Center for Biotechnology Information General Identifier No. 2499945, May 30, 2000, Nasr, F. et al., Heterospecific Cloning of *Arabidopsis thaliana* cDNAs by Direct Complementation of Pyrimidine Auxotrophic Mutants of *Saccharomyces cerevisiae*. I. Cloning and Sequence Analysis of two cDNAs Catalysing the second, fifth and sixth steps of the de novo Pyrimidine Biosynthesis Pathway.
Fahd Nasr et al., Mol. Gen. Genet. vol. 244:23–32, 1994, Heterospecific Cloning of *Arabidopsis thaliana* cDNAs by Direct Complementation of Pyrimidine Auxotrophic Mutants of *Saccharomyces cerevisiae*. I. Cloning and Sequence Analaysis of two cDNAs Catalysing the second, fifth and sixth steps of the de novo Pyrimidine Biosynthesis Pathway.
National Center for Biotechnology Information General Identifier No. 2499946, May 30, 2000, Maier, T. et al., Nucleotide Sequence ofa cDNA Encoding UMP Synthase from *Nicotiana tabacum*.
Ulrich Strych et al., Current Microbiology, vol. 29:353–359, 1994, Orotidine–5'–Monophosphate Decarboxylase from Pseudomonas Aeruginosa PAO1: Cloning, Overexpression, and Enzyme Characterization.
Kristen K. Seymour et al., Biochemistry, vol. 33:5268–5274, 1994, Cytotoxic Effects of Inhibitors of de Novo Pyrimidine Biosynthesis upon *Plasmodium falciparum*.

*Primary Examiner*—Phuong T. Bui

(57) ABSTRACT

This invention relates to an isolated nucleic acid fragment encoding an OMP decarboxylase. The invention also relates to the construction of a chimeric gene encoding all or a portion of the OMP decarboxylase, in sense or antisense orientation, wherein expression of the chimeric gene results in production of altered levels of the OMP decarboxylase in a transformed host cell.

11 Claims, 2 Drawing Sheets

| SEQ ID NO:6 | MTTPSLVESLVLQLHEISAVKFGNEFKLKSGIFSPIYTDLRLIISYPSLLQQISQTLISSV |
| SEQ ID NO:8 | MDAAAL-ESLILDLHAIEVVKLGSFTLKSGIKSPIYLDLRALVSHPRLLSAVA-SLLHAL |
| SEQ ID NO:10 | MDAAAL-ESLILDLHAIEVVKLGSFTLKSGIKSPIYLDLRALVSHPRLLSAVA-SLLHAL |
| SEQ ID NO:12 | MDAAA-QESLILELHAIEAIKFGTFVLKSGITSPIYLDLRALVSHPGLLSSIA-TLLHTL |
| SEQ. ID NO:13 | MSA----MEALILQLHEIGAVKFGNEFKLKSGIFSPVYIDLRLIVSYPSLLTQISQTLISSL |
| SEQ. ID NO:14 | -------DISAVKFGEFKLKSGISSPIYIDLRLIVSYPSILRQISQTLVGSL |

| SEQ ID NO:6 | -SSTSFDLVCGVPYTALPIATCVSLAQNIPMVMRRKEIKDYGTAKAIEGDFKPGQSCLII |
| SEQ ID NO:8 | PATRPYGLVCGVPYTALPIAAVLSVDRSIPMLMRRKEVKAHGTAKSIEGSFSPGDTVLII |
| SEQ ID NO:10 | PATRPYGLVCGVPYTALPIAAVLSVDRSIPMLMRRKEVKAHGTAKSIEGSFSPGDTVLII |
| SEQ ID NO:12 | PATRPYDLLCGVPYTALPIASVLSVHRSVPMVMRRKEAKAHGTAKSIEGAFRAGEAVLII |
| SEQ. ID NO:13 | PPSATFDVVCGVPYTALPIATVVSVSNGIPMLMRRKEIKDYGTSKAIEGIFEKDQTCLII |
| SEQ. ID NO:14 | PSSTKYDVVCGVPYTALPIATCISTAHDVPMLMRRKEVKDYGTAKAIEGAFKPGQACLIV |

| SEQ ID NO:6 | EDLVTSGTSVLETAAPLRAVGLKISDAVVLIDREQGGRENLEENGIKLHAIIKLTEMVKI |
| SEQ ID NO:8 | EDLVTSGASVLETAAPLRAEGLVVADAVVVVDREQGGRENLAANGITLHSLMTLTEVLAV |
| SEQ ID NO:10 | EDLVTSGASVLETAAPLRAEGLVVADAVVVVDREQGGRENLAANGITLHSLMTLTEVLAV |
| SEQ ID NO:12 | EDLVTSGASVLETAAPLRDQGLVVADAVVVVDRKQGGRENLAANGITLHSLMTLTEVLAV |
| SEQ. ID NO:13 | EDLVTSGASVLETAAPLRAVGLKVSDAVVLIDRQQGGRENLAENGIKLHSMIMLTDMVRV |
| SEQ. ID NO:14 | EDLVTSGASVLETAAPLRAAGLTVTDAVVMIDREQGGRENLAENGITLHSMVKLTEMVKI |

| SEQ ID NO:6 | LGNHGKLDEEMVGVVTKFLEDNRKVAALAKVEKPVTKVKALPFGERAKLSKNPMGKRLFE |
| SEQ ID NO:8 | LLKHGKVTEEKAQEVRQFLDANRKVAVPG-AAPVTPRVLRKTFSERANLATNPMGKKLFE |
| SEQ ID NO:10 | LLKHGKVTEEKAQEVRQFLDANRKVAVPG-AAPVTPRVLRKTFSERANLATNPMGKKLFE |
| SEQ ID NO:12 | LLKHGKVTQEERGG-KQFLDANRKVTVPGAAGAVKPKAVRKGFAERAGLAKNPMGKRLFE |
| SEQ. ID NO:13 | LKEKGKIEEVEVNLLKFLEENRRVSVPS-VEKPKPKPRVLGFKERSELSKNPTGKKLFD |
| SEQ. ID NO:14 | LKEKGRVSEETEKMVKKFLEENRKVAVPVKETKVSLR---LPYQERAKIAKNPTGKKLFE |

| SEQ ID NO:6 | IMAEKESNLCLAADVGTAAELLEIAEKVGPEICLLKTHVDIFPDFTADFGSKLLSIAEKH |
| SEQ ID NO:8 | LMETKQTNLCVAADVGTTKELLELADKVGPQICMLKTHVDILSDFTPDFGSKLRSIAEKH |
| SEQ ID NO:10 | LMETKQTNLCVAADVGTTKELLELADKVGPQICMLKTHVDILSDFTPDFGSKLRSIAEKH |
| SEQ ID NO:12 | VMEAKQSNLCVAADVGTAKELLELAEKVGPEICMLKTHVDILSDFTPDFGAKLRSIAEKH |
| SEQ. ID NO:13 | IMLKKETNLCLAADVGTAAELLDIADKVGPEICLLKTHVDILPDFTPDFGSKLRAIADKH |
| SEQ. ID NO:14 | IMVQKETNLCLSADVATAAELLDIADKVGPEICMLKTHVDILPDFTPDFGSKLRSIADKH |

FIG. 1A

| | |
|---|---|
| SEQ ID NO:6 | NFLIFEDRKFADIGNTVTMQYEGGVFRILDWAHIVNAHIISGPGIVDGLKLKGLPRGRGL |
| SEQ ID NO:8 | NFLIFEDRKFADIGNTVTMQYEGGIFRILDWADIVNAHIVPGPGIVDGLKLKGLPKGRGL |
| SEQ ID NO:10 | NFLIFEDRKFADIGNTVTMQYEGGIFRILDWADIVNAHIVPGPGIVDGLKLKGLPKGRGL |
| SEQ ID NO:12 | NFLIFEDRKFADIGNTVTMQYEGGIFRILDWADIVNAHIIPGPGIVDGLKLKGLPKGRGL |
| SEQ.ID NO:13 | KFLIFEDRKFADIGNTVTMQYEGGIFKILEWADIINAHVISGPGIVDGLKLKGMPRGRGL |
| SEQ.ID NO:14 | NFLIFEDRKFADIGNTVTMQYEGGIFRILDWADITNAHIISGPGIVDGLKLKGLSRGRGL |
| | |
| SEQ ID NO:6 | LLLAEMSSAGNLAKGDYTTSAVKIAEDHSDFVIGFISVNPASWPGAPINPSFIQATPGVQ |
| SEQ ID NO:8 | LLLAEMSSAGNLAHGDYTAAAVKIAEQHSDFVMGFISVNPESWSVKPSSPAFIHATPGVQ |
| SEQ ID NO:10 | LLLAEMSSAGNLAHGDYTAAAVKIAEQHSDFVMGFISVNPESWSVKPSSPAFIHATPGVQ |
| SEQ ID NO:12 | LLLAEMSSAGNLAHGEYTAAAVKIAEQHSDFVIGFISVNPASWSVAPSSPAFIHATPGVQ |
| SEQ.ID NO:13 | LLLAEMSSAGNLATGDYTAAAVKIADAHSDFVMGFISVNPASWKCGYVYPSMIHATPGVQ |
| SEQ.ID NO:14 | LLLAEMSSAGNLATGAYTAAAVKIAEDHSDFVIGFISVNPASWPNAPGNPSLIHATPGVQ |
| | |
| SEQ ID NO:6 | MVTGGDALGQQYNTPYSVIHDRGSDIIIVGRGIIKAANHAEIAREYRLQGWNAYLAKCN- |
| SEQ ID NO:8 | MVAGGDDLGQQYNTPESVINYRGSDIIIVGRGIIKASDPMKKAWEYRLQGWQAY-KNSLL |
| SEQ ID NO:10 | MVAGGDDLGQQYNTPESVINYRGSDIIIVGRGIIKASDPMKKAWEYRLQGWQAY-KNSLL |
| SEQ ID NO:12 | MVSGGDALGQQYNTPHSVINDK------RQVT------------------------- |
| SEQ.ID NO:13 | MVKGGDALGQQYNTPHSVITERGSDIIIVGRGIIKAENPAETAHEYRVQGWNAYLEKCSQ |
| SEQ.ID NO:14 | LVKGGDALGQLYNTPSAVIADRGSDIIIVGRGIIKAANPIEAAREYRLQGWDAYLVNCK- |

FIG. 1B

GENE INVOLVED IN PYRIMIDINE BIOSYNTHESIS IN PLANTS

This is Application claims priority benefit of U.S. Provisional Application No. 60/156,901, filed Sep. 30, 1999.

FIELD OF THE INVENTION

This invention is in the field of plant molecular biology. More specifically, this invention pertains to nucleic acid molecules coding for an enzyme involved in pyrimidine biosynthesis in plants, especially in seeds.

BACKGROUND OF THE INVENTION

Orotidine 5'-monophosphate decarboxylase (OMP decarboxylase) catalyzes the final reaction in pyrimidine nucleotide biosynthesis, converting OMP to uridine 5'-monophosphate (UMP). In eukaryotes, this enzyme also performs the next-to-last step of linking phosphoribosyl-pyrophosphate (PRPP) to orotate to form OMP (Reyes and Guganig (1975) *J Biol Chem* 250:5097–108; Traut et al. (1980) *Biochemistry* 19:6062–8). The enzyme is a target for feedback inhibition wherein UTP and UMP both reduce its activity. In prokaryotes, in contrast, there is no feedback inhibition, and and the last two enzymatic reactions are not coupled.

Nucleotides are required for the synthesis of DNA and RNA, and are indirectly responsible for protein synthesis, due to the requirement for ribosomes and tRNAs in translation. Therefore, pyrimidine biosynthesis is a key metabolic pathway in all eukaryotes. Manipulation of this pathway is neverthelss possible since mutations to key enzymes can be partially overcome by feeding cells having potentially lethal mutations with CTP, UTP, or their mono- or diphosphate derivatives. Inhibitors of OMP decarboxylase have been identified which vary in their efficacy among different organisms, implying that engineering of the active site may yield enzymes that are more or less sensitive to inhibition (Shostak and Jones (1992) *Biochemistry* 31:12155–61). It is believed that overexpression or inhibition of OMP decarboxylase in plants may be useful for enhancing growth rates, developing new herbicides, developing new fungicides, developing new insecticides, or selectively altering development of individual organs.

SUMMARY OF THE INVENTION

The present invention concerns an isolated polynucleotide comprising a nucleotide sequence selected from the group consisting of: (a) a first nucleotide sequence encoding a polypeptide of at least 200 amino acids having at least 85% identity based on the Clustal method of alignment when compared to a polypeptide selected from the group consisting of SEQ ID NOs:2, 4, 6, 8, 10, and 12, or (b) a second nucleotide sequence comprising the complement of the first nucleotide sequence.

In a second embodiment, it is preferred that the isolated polynucleotide of the claimed invention comprises a first nucleotide sequence which comprises a nucleic acid sequence selected from the group consisting of SEQ ID NOs:1, 3, 5, 7, 9, and 11 that codes for the polypeptide selected from the group consisting of SEQ ID NOs:2, 4, 6, 8, 10, and 12.

In a third embodiment, this invention concerns an isolated polynucleotide comprising a nucleotide sequence of at least one of 800 (preferably at least one of 500, most preferably at least one of 400) contiguous nucleotides derived from a nucleotide sequence selected from the group consisting of SEQ ID NOs:1, 3, 5, 7, 9, and 11 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

In a seventh embodiment, the invention concerns an OMP decarboxylase polypeptide of at least 200 amino acids comprising at least 85% identity based on the Clustal method of alignment compared to a polypeptide selected from the group consisting of SEQ ID NOs:2, 4, 6, 8, 10, and 12.

In an eighth embodiment, the invention relates to a method of selecting an isolated polynucleotide that affects the level of expression of an OMP decarboxylase polypeptide or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the OMP decarboxylase polypeptide or enzyme activity in the host cell containing the isolated polynucleotide; and (d) comparing the level of the OMP decarboxylase polypeptide or enzyme activity in the host cell containing the isolated polynucleotide with the level of the OMP decarboxylase polypeptide or enzyme activity in the host cell that does not contain the isolated polynucleotide.

In a ninth embodiment, the invention concerns a method of obtaining a nucleic acid fragment encoding a substantial portion of an OMP decarboxylase polypeptide, preferably a plant OMP decarboxylase polypeptide, comprising the steps of: synthesizing an oligonucleotide primer comprising a nucleotide sequence of at least one of 800 (preferably at least one of 500, most preferably at least one of 400) contiguous nucleotides derived from a nucleotide sequence selected from the group consisting of SEQ ID NOs:1, 3, 5, 7, 9, and 11, and the complement of such nucleotide sequences; and amplifying a nucleic acid fragment (preferably a cDNA inserted in a cloning vector) using the oligonucleotide primer. The amplified nucleic acid fragment preferably will encode a substantial portion of an OMP decarboxylase amino acid sequence.

In a tenth embodiment, this invention relates to a method of obtaining a nucleic acid fragment encoding all or a substantial portion of the amino acid sequence encoding an OMP decarboxylase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide of the present invention.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the OMP decarboxylase polynucleotide in an amount sufficient to complement a null mutant to provide a positive selection means.

In a thirteenth embodiment, this invention relates to a method of altering the level of expression of an OMP decarboxylase in a host cell comprising: (a) transforming a host cell with a chimeric gene of the present invention; and (b) growing the transformed host cell under conditions that are suitable for expression of the chimeric gene wherein expression of the chimeric gene results in production of altered levels of the OMP decarboxylase in the transformed host cell.

A further embodiment of the instant invention is a method for evaluating at least one compound for its ability to inhibit the activity of an enzyme involved in primidine biosynthesis, the method comprising the steps of: (a) transforming a host cell with a chimeric gene comprising a nucleic acid fragment encoding an OMP decarboxylase polypeptide, operably linked to suitable regulatory sequences; (b) growing the transformed host cell under conditions that are suitable for expression of the chimeric gene wherein expression of the chimeric gene results in production of an OMP decarboxylase in the transformed host cell; (c) optionally purifying the OMP decarboxylase polypeptide expressed by the transformed host cell; (d) treating the OMP decarboxylase polypeptide with a compound to be tested; and (e) comparing the activity of the OMP decarboxylase polypeptide that has been treated with a test compound to the activity of an untreated OMP decarboxylase polypeptide, thereby selecting compounds with potential for inhibitory activity.

BRIEF DESCRIPTION OF THE DRAWINGS AND SEQUENCE LISTINGS

The invention can be more fully understood from the following detailed description and the accompanying drawings and Sequence Listing which form a part of this application.

FIGS. 1(1A–1B) shows a comparison of the amino acid sequences set forth in SEQ ID NOs:6, 8, 10, and 12, and the *Arabidopsis thaliana* and *Nicotiana tabacum* (NCBI General Identifier No. gi 2499945 and gi 2499946, respectively) sequences (SEQ ID NOs:13 and 14, respectively).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Orotidine-5-Phosphate Decarboxylase

| | | SEQ ID NO: | |
|---|---|---|---|
| Protein | Clone Designation | (Nucleotide) | (Amino Acid) |
| Corn OMP Decarboxylase | p0127.cntbe57r | 1 | 2 |
| Rice OMP Decarboxylase | rsl1n.pk004.j19 | 3 | 4 |
| Soybean OMP Decarboxylase | sfl1.pk135.i17 | 5 | 6 |
| Wheat OMP Decarboxylase | wl1n.pk0029.c7 | 7 | 8 |
| Corn OMP Decarboxylase | p0127.cntbe57r:fis | 9 | 10 |
| Rice OMP Decarboxylase | rsl1n.pk004.j19:fis | 11 | 12 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 800 contiguous nucleotides, preferably at least one of 40 contiguous nucleotides, most preferably one of at least 30 contiguous nucleotides derived from SEQ ID NOs:1, 3, 5, 7, 9, and 11, or the complement of such sequences.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 800 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 800 (preferably at least one of 500, most preferably at least one of 400) contiguous nucleotides derived from a nucleotide sequence selected from the group consisting of SEQ ID NOs:1, 3, 5, 7, 9, and 11, and the complement of such nucleotide sequences may be used in methods of selecting an isolated polynucleotide that affects the expression of an OMP decarboxylase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences disclosed herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) first nucleotide sequence encoding a polypeptide of at least 200 amino acids having at least 85% identity based on the Clustal method of alignment when compared to a polypeptide selected from the group consisting of SEQ ID NOs:2, 4, 6, 8, 10, and 12, or (b) a second nucleotide sequence comprising the complement of the first nucleotide sequence.

Preferably, the first nucleotide sequence comprises a nucleic acid sequence selected from the group consisting of SEQ ID NOs:1, 3, 5, 7, 9, and 11, that codes for the polypeptide selected from the group consisting of SEQ ID NOs:2, 4, 6, 8, 10, and 12.

Nucleic acid fragments encoding at least a portion of several OMP decarboxylase have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other OMP decarboxylase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 800 (preferably one of at least 500, most preferably one of at least 400) contiguous nucleotides derived from a nucleotide sequence selected from the group consisting of SEQ ID NOs:1, 3, 5, 7, 9, and 11 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of an OMP decarboxylase polypeptide, preferably a substantial portion of a plant OMP decarboxylase polypeptide, comprising the steps of: synthesizing an oligonucleotide primer comprising a nucleotide sequence of at least one of 800 (preferably at least one of 500, most preferably at least one of 400) contiguous nucleotides derived from a nucleotide sequence selected from the group consisting of SEQ ID NOs:1, 3, 5, 7, 9, and 11, and the complement of such nucleotide sequences; and amplifying a nucleic acid fragment (preferably a cDNA inserted in a cloning vector) using the oligonucleotide primer. The amplified nucleic acid fragment preferably will encode a portion of an OMP decarboxylase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of pyrimidine biosynthesis or metabolism in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 200 amino acids that has at least 85% identity based on the Clustal method of alignment when compared to a polypeptide selected from the group consisting of SEQ ID NOs:2, 4, 6, 8, 10, and 12.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded OMP decarboxylase. An example of a vector for high level expression of the instant polypeptides in a bacterial host is provided (Example 6).

Additionally, the instant polypeptides can be used as a target to facilitate design and/or identification of inhibitors of those enzymes that may be useful as herbicides. This is desirable because the polypeptides described herein catalyze a key step in pyrimidine biosynthesis. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear, and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries: Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| p0127 | Nucellus tissue, 5 days after silking, screened 1 | p0127.cntbe57r |
| rsl1n | Rice (*Oryza sativa*, YM) 15 day old seedling normalized* | rsl1n.pk004.j19 |
| sfl1 | Soybean Immature Flower | sfl1.pk135.i17 |
| wl1n | Wheat Leaf From 7 Day Old Seedling* | wl1n.pk0027.c7 |
| p0127 | Nucellus tissue, 5 days after silking, screened 1 | p0127.cntbe47r:fis |

TABLE 2-continued cDNA Libraries from Corn, Rice, Soybean, and Wheat

| Library | Tissue | Clone |
|---|---|---|
| rsl1n | Rice (*Oryza sativa*, YM) 15 day old seedling normalized* | rsl1n.pk004.j19:fis |
| sfl1 | Soybean Immature Flower | sfl1.pk135.i17:fis |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding OMP decarboxylase were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402. ) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding OMP Decarboxylase

The BLASTX search using the EST sequences from clones listed in Table 3 revealed similarity of the polypeptides encoded by the cDNAs to OMP decarboxylase from *Arabidopsis thaliana* and *Nicotiana tabacum* (NCBI General Identifier No. gi 2499945 and gi 2499946, respectively). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding Polypeptides Homologous to OMP Decarboxylase

| Clone | Status | BLAST pLog Score gi2599945 | gi2499946 |
|---|---|---|---|
| p0127.cntbe57r | EST | 25.70 | |
| rsl1n.pk004.j19 | EST | 37.70 | |
| sfl1.pk135.i17 | EST | >180.00 | |
| wl1n.pk0029.c7 | FIS | | 167.00 |

The sequence of the entire cDNA insert in the clones listed in Table 3 was determined. Further sequencing and searching of the DuPont proprietary database allowed the identification of other corn, rice, soybean and/or wheat clones encoding OMP decarboxylase. The BLASTX search using the EST sequences from clones listed in Table 4 revealed similarity of the polypeptides encoded by the cDNAs to OMP decarboxylase from *Arabidopsis thaliana* (NCBI General Identifier No. gi 2599945). Shown in Table 4 are the BLAST results for individual ESTs ("EST"), the sequences of the entire cDNA inserts comprising the indicated cDNA clones ("FIS"), sequences of contigs assembled from two or more ESTs ("Contig"), sequences of contigs assembled from an FIS and one or more ESTs ("Contig*"), or sequences encoding the entire protein derived from an FIS, a contig, or an FIS and PCR ("CGS"):

TABLE 4

BLAST Results for Sequences Encoding Polypeptides Homologous to OMP Decarboxylase

| Clone | Status | BLAST pLog Score gi2599945 |
|---|---|---|
| p0127.cntbe57r:fis | FIS | >180.00 |
| rsl1n.pk004.j19:fis | CGS | 172.00 |

FIG. 1 presents an alignment of the amino acid sequences set forth in SEQ ID NOs:6, 8, 10, and 12, and the *Arabidopsis thaliana* and *Nicotiana tabacum* (NCBI General Identifier No. gi 2499945 and gi 2499946, respectively) sequences (SEQ ID NOs:13 and 14, respectively). The data in Table 5 represents a calculation of the percent identity of the amino acid sequences set forth in SEQ ID NOs:2, 4, 6, 8, 10, and 12, and the *Arabidopsis thaliana* and *Nicotiana tabacum* (NCBI General Identifier No. gi 2499945 and gi 2499946, respectively) sequences (SEQ ID NOs:13 and 14, respectively).

TABLE 5

Percent Identity of Amino Acid Sequences Deduced From the Nucleotide Sequences of cDNA Clones Encoding Polypeptides Homologous to OMP Decarboxylase

| | Percent Identity to | |
|---|---|---|
| SEQ ID NO. | gi2599945 | gi2499946 |
| 2 | 52.6% | |
| 4 | 79.5% | |
| 6 | 75.6% | |
| 8 | | 69.2% |
| 10 | 67.0% | |
| 12 | 65.7% | |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a OMP decarboxylase. These sequences represent the first corn, soybean, and wheat sequences encoding OMP decarboxylase known to Applicant.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein et al. (1987) Nature 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M-solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of OMP Decarboxylase The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for OMP decarboxylase are presented by Strych et al. (1994) *Curr Microbiol* 29:353–9; Seymour et al. (1994) *Biochemistry* 33:5268–74; Shostak and Jones (1992) *Biochemistry* 31:12155–61; and Traut et al. (1980) *Biochemistry* 19:6062–8.

What is claimed is:

1. An isolated polynucleotide comprising:
   (a) a nucleotide sequence encoding a polypeptide having OMP decarboxylase activity, wherein the polypeptide has an amino acid sequence of at least 90% sequence identity based on Clustal alignment method when compared to SEQ ID NO:10, or
   (b) the complement of the nucleotide sequence of (a), wherein the complement and the nucleotide sequence contain the same number of nucleotides and are 100% complementary.

2. The polynucleotide of claim 1, wherein the polypeptide has an amino acid sequence of at least 95% sequence identity based on Clustal alignment method when compared to SEQ ID NO:10.

3. The polynucleotide of claim 1, wherein the amino acid sequence of the polypeptide comprises SEQ ID NO:10.

4. The polynucleotide of claim 1, wherein the nucleotide sequence of the polynucleotide comprises SEQ ID NO:9.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *

SEQUENCE LISTING

```
<160> NUMBER OF SEQ ID NOS: 14

<210> SEQ ID NO 1
<211> LENGTH: 510
<212> TYPE: DNA
<213> ORGANISM: Zea mays
<220> FEATURE:
<221> NAME/KEY: unsure
<222> LOCATION: (9)
<223> OTHER INFORMATION: n = A, C, G or T
<220> FEATURE:
<221> NAME/KEY: unsure
<222> LOCATION: (238)
<223> OTHER INFORMATION: n = A, C, G or T
<220> FEATURE:
<221> NAME/KEY: unsure
<222> LOCATION: (262)
<223> OTHER INFORMATION: n = A, C, G or T
<220> FEATURE:
<221> NAME/KEY: unsure
<222> LOCATION: (322)
<223> OTHER INFORMATION: n = A, C, G or T
<220> FEATURE:
<221> NAME/KEY: unsure
<222> LOCATION: (349)
<223> OTHER INFORMATION: n = A, C, G or T
<220> FEATURE:
<221> NAME/KEY: unsure
<222> LOCATION: (352)
<223> OTHER INFORMATION: n = A, C, G or T
<220> FEATURE:
<221> NAME/KEY: unsure
<222> LOCATION: (406)
<223> OTHER INFORMATION: n = A, C, G or T
<220> FEATURE:
<221> NAME/KEY: unsure
<222> LOCATION: (452)
<223> OTHER INFORMATION: n = A, C, G or T
<220> FEATURE:
<221> NAME/KEY: unsure
<222> LOCATION: (459)
<223> OTHER INFORMATION: n = A, C, G or T
<220> FEATURE:
<221> NAME/KEY: unsure
<222> LOCATION: (476)..(477)
<223> OTHER INFORMATION: n = A, C, G or T
<220> FEATURE:
<221> NAME/KEY: unsure
<222> LOCATION: (486)
<223> OTHER INFORMATION: n = A, C, G or T
```

<400> SEQUENCE: 1

```
gtacaaagnc acttcctgct ctcgctccgc cgccgccgcc tccctcccca gtcgatcacc    60
aaacctcagt ccaaactcca aaccccgcc gcatcagaaa aaaaccctag gccatggacg    120
ccgcggcgct ggagtcgctc atcctggacc tccacgccat cgaggtcgtg aagctgggct    180
ccttcacgct caagtccggc atcaaatcgc ccatctacct cgacctccgc gcgctcgnct    240
cccacccgcg cctgctctcc gncgtcgcct cgctccttca cgcgctcccg ccacgcgcc    300 cctacggcct cgtctgcggt gncccctaca ccgcgctccc catcgccgnc gncctctccg    360
tcgaccgctc aatccccatg ctcatgcgcc gcaaggaggt caaggnccac ggaccgcaag    420
tccatcgagg gctcttcagc cggggacacc gnctatatng agactcgcac agtggnnctc    480
ggctcngacg cgccgtcggc gagggctgcg                                    510
```

<210> SEQ ID NO 2
<211> LENGTH: 97
<212> TYPE: PRT
<213> ORGANISM: Zea mays
<220> FEATURE:
<221> NAME/KEY: UNSURE
<222> LOCATION: (39)
<223> OTHER INFORMATION: Xaa = ANY AMINO ACID
<220> FEATURE:
<221> NAME/KEY: UNSURE
<222> LOCATION: (47)
<223> OTHER INFORMATION: Xaa = ANY AMINO ACID
<220> FEATURE:
<221> NAME/KEY: UNSURE
<222> LOCATION: (67)
<223> OTHER INFORMATION: Xaa = ANY AMINO ACID
<220> FEATURE:
<221> NAME/KEY: UNSURE
<222> LOCATION: (76)..(77)
<223> OTHER INFORMATION: Xaa = ANY AMINO ACID
<220> FEATURE:
<221> NAME/KEY: UNSURE
<222> LOCATION: (95)
<223> OTHER INFORMATION: Xaa = ANY AMINO ACID

<400> SEQUENCE: 2

```
Ala Ala Leu Glu Ser Leu Ile Leu Asp Leu His Ala Ile Glu Val Val
 1               5                  10                  15

Lys Leu Gly Ser Phe Thr Leu Lys Ser Gly Ile Lys Ser Pro Ile Tyr
             20                  25                  30

Leu Asp Leu Arg Ala Leu Xaa Ser His Pro Arg Leu Leu Ser Xaa Val
         35                  40                  45

Ala Ser Leu Leu His Ala Leu Pro Ala Thr Arg Pro Tyr Gly Leu Val
     50                  55                  60

Cys Gly Xaa Pro Tyr Thr Ala Leu Pro Ile Ala Xaa Xaa Leu Ser Val
 65                  70                  75                  80

Asp Arg Ser Ile Pro Met Leu Met Arg Arg Lys Glu Val Lys Xaa His
                 85                  90                  95

Gly
 97
```

<210> SEQ ID NO 3
<211> LENGTH: 514
<212> TYPE: DNA
<213> ORGANISM: Oryza sativa
<220> FEATURE:
<221> NAME/KEY: unsure
<222> LOCATION: (376)
<223> OTHER INFORMATION: n = A, C, G or T
<220> FEATURE:

```
<221> NAME/KEY: unsure
<222> LOCATION: (384)
<223> OTHER INFORMATION: n = A, C, G or T
<220> FEATURE:
<221> NAME/KEY: unsure
<222> LOCATION: (407)
<223> OTHER INFORMATION: n = A, C, G or T
<220> FEATURE:
<221> NAME/KEY: unsure
<222> LOCATION: (445)
<223> OTHER INFORMATION: n = A, C, G or T
<220> FEATURE:
<221> NAME/KEY: unsure
<222> LOCATION: (452)..(453)
<223> OTHER INFORMATION: n = A, C, G or T
<220> FEATURE:
<221> NAME/KEY: unsure
<222> LOCATION: (472)
<223> OTHER INFORMATION: n = A, C, G or T
<220> FEATURE:
<221> NAME/KEY: unsure
<222> LOCATION: (474)
<223> OTHER INFORMATION: n = A, C, G or T
<220> FEATURE:
<221> NAME/KEY: unsure
<222> LOCATION: (486)
<223> OTHER INFORMATION: n = A, C, G or T
<220> FEATURE:
<221> NAME/KEY: unsure
<222> LOCATION: (499)
<223> OTHER INFORMATION: n = A, C, G or T
<220> FEATURE:
<221> NAME/KEY: unsure
<222> LOCATION: (509)
<223> OTHER INFORMATION: n = A, C, G or T

<400> SEQUENCE: 3
ctgcttttgc ttgctgaaat gagctcggct ggcaaccttg ctcatggaga gtacactgct      60
gcagctgtaa agattgctga gcaacattct gattttgtaa ttggatttat atccgttaat     120
ccagcatctt ggtcagttgc gccatcaagt ccagcattta tccatgccac tcctggagtg     180
cagatggttt ctggaggaga tgctcttggt caacagtaca ataccectca ttctgttata     240 aacgacaaga ggcaagtgac ataattatag tccggacgag ggattataaa ggcgaagtaa     300
tccagcccga daccgcgagg gaagtaccgc atccaagggt gggggagcaa acaatccag      360 ctttgccatg agaaantgag aatngtgttt aggcaatggt tggttcnagc ttatgattta     420
ttataaccaa gaataattaa gccangattg cnnataaagc cgggattaat antnaagctg     480
ccatanaaat aaactgtgna gttggttgnt ttgg                                 514

<210> SEQ ID NO 4
<211> LENGTH: 83
<212> TYPE: PRT
<213> ORGANISM: Oryza sativa

<400> SEQUENCE: 4

Leu Leu Leu Leu Ala Glu Met Ser Ser Ala Gly Asn Leu Ala His Gly
 1               5                  10                  15

Glu Tyr Thr Ala Ala Ala Val Lys Ile Ala Glu Gln His Ser Asp Phe
            20                  25                  30

Val Ile Gly Phe Ile Ser Val Asn Pro Ala Ser Trp Ser Val Ala Pro
        35                  40                  45

Ser Ser Pro Ala Phe Ile His Ala Thr Pro Gly Val Gln Met Val Ser
    50                  55                  60

Gly Gly Asp Ala Leu Gly Gln Gln Tyr Asn Thr Pro His Ser Val Ile
65                  70                  75                  80
```

Asn Asp Lys
        83

<210> SEQ ID NO 5
<211> LENGTH: 1730
<212> TYPE: DNA
<213> ORGANISM: Glycine max

<400> SEQUENCE: 5

| | | | | | |
|---|---|---|---|---|---|
| gcacgaggtt | ttcctttact | ggtaagttgt | aaccctataa | gccgttgctc | ccaccgccgc | 60 |
| cgcgcagatc | tccgtttcaa | cttgggttat | ctctaaggtc | ctaaacaatc | ctctttcaaa | 120 |
| aacataccga | gaaagtgtg | gaaatgacga | caccatcatt | ggtagagtct | ctagttcttc | 180 |
| aactccatga | gatctcagct | gtcaaatttg | gcaacttcaa | gctcaaatct | ggcatcttct | 240 |
| caccaatcta | catagacctc | cgcctcatca | tatcttaccc | ttctctcctc | caacagatct | 300 |
| ctcaaaccct | tatttcttca | gtctcttcca | cttcctttga | cctcgtatgc | ggtgtccctt | 360 |
| acactgcctt | acccattgct | acatgtgtct | ctcttgctca | gaacattccc | atggtcatgc | 420 |
| gccgcaaaga | aatcaaagat | tatggcactg | ctaaagctat | tgaaggcgat | tcaagcctg  | 480 |
| gccaaagttg | cttaatcatt | gaggatttgg | ttaccagtgg | cacgtcagtt | ttggaaactg | 540 |
| cggcgccatt | gcgtgctgtg | ggattaaaga | tcagtgatgc | tgttgtgttg | atcgatagag | 600 |
| agcaaggtgg | cagagaaaac | ttggaggaga | atggcatcaa | gctgcatgca | attattaaat | 660 |
| tgactgaaat | ggtgaaaatt | ttgggcaatc | acgggaagct | tgatgaagag | atggtagggg | 720 |
| ttgttacgaa | gttcttagag | gataatcgta | aggttgctgc | tttggcaaag | gtggagaagc | 780 |
| ctgtaactaa | ggtcaaagct | ttgccatttg | gggagagggc | taagctgtcg | aagaatccaa | 840 |
| tgggaaagag | gttgtttgag | ataatggctg | agaaggagag | taatctatgt | ttggctgctg | 900 |
| atgttggaac | tgcagctgaa | ttgcttgaaa | ttgctgagaa | ggttggacct | gagatatgct | 960 |
| tgctgaagac | tcatgtggat | attttccag  | attttactgc | tgattttggc | tctaagcttc | 1020 |
| tctcgattgc | agaaaaacat | aacttcttaa | tctttgagga | tcgtaaattt | gctgatattg | 1080 |
| gcaacacagt | gaccatgcaa | tatgaaggag | gggttttcg  | tatattggat | tgggctcata | 1140 |
| tagtaaatgc | tcacataatc | tcaggtcctg | gaattgttga | tggattaaaa | ttgaagggtt | 1200 |
| tacctcgtgg | tagggtcta  | ttactgcttg | ctgaaatgag | ctcagctggt | aaccttgcca | 1260 |
| agggagatta | tacaacttct | gcagtaaaaa | ttgctgagga | tcattctgac | tttgtaattg | 1320 |
| gcttcatctc | agtcaatcct | gcatcatggc | caggggcacc | aataaatcct | tctttcattc | 1380 |
| aagcaacccc | tggagttcaa | atggtaactg | gtggcgatgc | tttagggcag | caatataaca | 1440 |
| ctccatattc | tgtgatccat | gatagggca  | gtgacatcat | catcgtggga | cgtggcatca | 1500 |
| tcaaagcagc | aaaccatgct | gagatagctc | gtgaatatcg | tcttcaagga | tggaatgcat | 1560 |
| atttggctaa | atgtaattga | tgcctgcatt | cctagaataa | aattatgagc | ttaaattatg | 1620 |
| ttttaatggg | acatctgatc | tcactgtaac | ccagatgaat | aaggtcttgg | ggtacaatat | 1680 |
| gaagacattt | ttcggttgga | atattgaaaa | aaaaaaaaa  | aaaaaaaaa  |            | 1730 |

<210> SEQ ID NO 6
<211> LENGTH: 478
<212> TYPE: PRT
<213> ORGANISM: Glycine max

<400> SEQUENCE: 6

Met Thr Thr Pro Ser Leu Val Glu Ser Leu Val Leu Gln Leu His Glu
 1               5                  10                  15

-continued

```
Ile Ser Ala Val Lys Phe Gly Asn Phe Lys Leu Lys Ser Gly Ile Phe
             20                  25                  30
Ser Pro Ile Tyr Ile Asp Leu Arg Leu Ile Ile Ser Tyr Pro Ser Leu
         35                  40                  45
Leu Gln Gln Ile Ser Gln Thr Leu Ile Ser Ser Val Ser Ser Thr Ser
     50                  55                  60
Phe Asp Leu Val Cys Gly Val Pro Tyr Thr Ala Leu Pro Ile Ala Thr
 65                  70                  75                  80
Cys Val Ser Leu Ala Gln Asn Ile Pro Met Val Met Arg Arg Lys Glu
                 85                  90                  95
Ile Lys Asp Tyr Gly Thr Ala Lys Ala Ile Glu Gly Asp Phe Lys Pro
            100                 105                 110
Gly Gln Ser Cys Leu Ile Ile Glu Asp Leu Val Thr Ser Gly Thr Ser
        115                 120                 125
Val Leu Glu Thr Ala Ala Pro Leu Arg Ala Val Gly Leu Lys Ile Ser
    130                 135                 140
Asp Ala Val Val Leu Ile Asp Arg Glu Gln Gly Gly Arg Glu Asn Leu
145                 150                 155                 160
Glu Glu Asn Gly Ile Lys Leu His Ala Ile Ile Lys Leu Thr Glu Met
                165                 170                 175
Val Lys Ile Leu Gly Asn His Gly Lys Leu Asp Glu Glu Met Val Gly
            180                 185                 190
Val Val Thr Lys Phe Leu Glu Asp Asn Arg Lys Val Ala Ala Leu Ala
        195                 200                 205
Lys Val Glu Lys Pro Val Thr Lys Val Lys Ala Leu Pro Phe Gly Glu
    210                 215                 220
Arg Ala Lys Leu Ser Lys Asn Pro Met Gly Lys Arg Leu Phe Glu Ile
225                 230                 235                 240
Met Ala Glu Lys Glu Ser Asn Leu Cys Leu Ala Ala Asp Val Gly Thr
                245                 250                 255
Ala Ala Glu Leu Leu Glu Ile Ala Glu Lys Val Gly Pro Glu Ile Cys
            260                 265                 270
Leu Leu Lys Thr His Val Asp Ile Phe Pro Asp Phe Thr Ala Asp Phe
        275                 280                 285
Gly Ser Lys Leu Leu Ser Ile Ala Glu Lys His Asn Phe Leu Ile Phe
    290                 295                 300
Glu Asp Arg Lys Phe Ala Asp Ile Gly Asn Thr Val Thr Met Gln Tyr
305                 310                 315                 320
Glu Gly Gly Val Phe Arg Ile Leu Asp Trp Ala His Ile Val Asn Ala
                325                 330                 335
His Ile Ile Ser Gly Pro Gly Ile Val Asp Gly Leu Lys Leu Lys Gly
            340                 345                 350
Leu Pro Arg Gly Arg Gly Leu Leu Leu Leu Ala Glu Met Ser Ser Ala
        355                 360                 365
Gly Asn Leu Ala Lys Gly Asp Tyr Thr Thr Ser Ala Val Lys Ile Ala
    370                 375                 380
Glu Asp His Ser Asp Phe Val Ile Gly Phe Ile Ser Val Asn Pro Ala
385                 390                 395                 400
Ser Trp Pro Gly Ala Pro Ile Asn Pro Ser Phe Ile Gln Ala Thr Pro
                405                 410                 415
Gly Val Gln Met Val Thr Gly Gly Asp Ala Leu Gly Gln Gln Tyr Asn
            420                 425                 430
```

```
Thr Pro Tyr Ser Val Ile His Asp Arg Gly Ser Asp Ile Ile Ile Val
        435                 440                 445

Gly Arg Gly Ile Ile Lys Ala Ala Asn Pro Ala Glu Ile Ala Arg Glu
    450                 455                 460

Tyr Arg Leu Gln Gly Trp Asn Ala Tyr Leu Ala Lys Cys Asn
465                 470                 475

<210> SEQ ID NO 7
<211> LENGTH: 1781
<212> TYPE: DNA
<213> ORGANISM: Triticum aestivum

<400> SEQUENCE: 7
gcacgagtct cgctccgccg ccgccgcctc cctccccagt cgatcaccaa acctcagtcc    60
aaactccaaa cccccgccgc atcagaaaaa aaccctaggc catggacgcc gcggcgctgg   120
agtcgctcat cctggacctc cacgccatcg aggtcgtgaa gctgggctcc ttcacgctca   180
agtccggcat caaatcgccc atctacctcg acctccgcgc gctcgtctcc cacccgcgcc   240
tgctctccgc cgtcgcctcg ctccttcacg cgctcccggc cacgcgcccc tacggcctcg   300
tctgcggtgt ccctacacc gcgctcccca tcgccgccgt cctctccgtc gaccgctcaa   360
tccccatgct catgcgccgc aaggaggtca aggcccacgg caccgccaag tccatcgagg   420
gctccttcag ccccggggac accgtcctca tcatcgagga cctcgtcacc agtggcgcct   480
ccgtgctcga ccgccgcc ccgctccgcg ccgaggggct cgtcgtcgcc gacgccgtag   540
tcgtcgtcga ccgcgagcag ggtggcaggg agaacctcgc cgctaatggg atcacgctgc   600
actcgctcat gaccctcacg gaggtgctgg ccgtgctgct caagcacggg aaggtgaccg   660
aggagaaggc gcaggaggtg aggcagttcc tcgacgccaa caggaaggtg gcggtgcctg   720
gggcagcacc tgttcacccc agggtgctca gaaagacatt ttcggagagg gcgaatcttg   780
ccaccaaccc tatggggaag aagctcttcg agctgatgga gaccaagcag accaacctgt   840
gtgttgccgc tgatgtcggg acaacaaagg aactccttga gctggctgac aaggtcggcc   900
ctcaaatttg tatgttgaaa accatgtgg atatattatc tgattttacc ccagattttg   960
gctctaagct ccgctcgatt gctgagaagc acaactttt gatcttcgaa gaccgcaagt  1020
tgctgacat tggaaataca gtaaccatgc aatatgaagg aggaatattc cgcatattgg  1080
attgggccga tattgttaat gcgcatatag tacctggacc tggaatcgta gatggcttga  1140
agctgaaggg tttgcctaaa ggaagagggc tacttctgct cgctgagatg agctctgccg  1200
gcaaccttgc ccatggagat tacactgctg ctgccgtaaa gattgctgag caacattctg  1260
attttgtgat gggatttata tcagtaaatc ctgagtcttg gtcagtaaaa ccatcaagcc  1320
ctgcatttat ccatgccacg cctggagttc agatggtcgc aggaggagat gatcttgggc  1380
aacaatacaa cactcccgaa tctgtgataa actacagggg cagtgacata atcatagttg  1440
gccgtgggat tataaaggcg agcgatccta tgaagaaggc gtgggagtac cgcttgcaag  1500
ggtggcagga atacaagaac agcttgctat gaaggaaggg gggcgccatg agcatcccca  1560
agtataaggg cgaatccagt cagtttggcg aaataagcgc atgcggaaag gttttcctgc  1620
agttgagtca ggacctaatt gacatcagat tcactgcaga ggagactcat gccccatcat  1680
cgtttctgtt acaataattt cctctcggtt taccctgttc ttgctggttg agttaggcac  1740
gttgtgatgc ctgtgcgcgg ttaaaaaaaa aaaaaaaaa a                       1781

<210> SEQ ID NO 8
```

```
<211> LENGTH: 476
<212> TYPE: PRT
<213> ORGANISM: Triticum aestivum

<400> SEQUENCE: 8

Met Asp Ala Ala Leu Glu Ser Leu Ile Leu Asp Leu His Ala Ile
 1               5                  10                  15

Glu Val Val Lys Leu Gly Ser Phe Thr Leu Lys Ser Gly Ile Lys Ser
                20                  25                  30

Pro Ile Tyr Leu Asp Leu Arg Ala Leu Val Ser His Pro Arg Leu Leu
             35                  40                  45

Ser Ala Val Ala Ser Leu Leu His Ala Leu Pro Ala Thr Arg Pro Tyr
         50                  55                  60

Gly Leu Val Cys Gly Val Pro Tyr Thr Ala Leu Pro Ile Ala Ala Val
 65                  70                  75                  80

Leu Ser Val Asp Arg Ser Ile Pro Met Leu Met Arg Lys Glu Val
                 85                  90                  95

Lys Ala His Gly Thr Ala Lys Ser Ile Glu Gly Ser Phe Ser Pro Gly
                100                 105                 110

Asp Thr Val Leu Ile Ile Glu Asp Leu Val Thr Ser Gly Ala Ser Val
            115                 120                 125

Leu Glu Thr Ala Ala Pro Leu Arg Ala Glu Gly Leu Val Val Ala Asp
        130                 135                 140

Ala Val Val Val Asp Arg Glu Gln Gly Gly Arg Glu Asn Leu Ala
145                 150                 155                 160

Ala Asn Gly Ile Thr Leu His Ser Leu Met Thr Leu Thr Glu Val Leu
                165                 170                 175

Ala Val Leu Leu Lys His Gly Lys Val Thr Glu Lys Ala Gln Glu
            180                 185                 190

Val Arg Gln Phe Leu Asp Ala Asn Arg Lys Val Ala Val Pro Gly Ala
        195                 200                 205

Ala Pro Val Thr Pro Arg Val Leu Arg Lys Thr Phe Ser Glu Arg Ala
    210                 215                 220

Asn Leu Ala Thr Asn Pro Met Gly Lys Lys Leu Phe Glu Leu Met Glu
225                 230                 235                 240

Thr Lys Gln Thr Asn Leu Cys Val Ala Ala Asp Val Gly Thr Thr Lys
                245                 250                 255

Glu Leu Leu Glu Leu Ala Asp Lys Val Gly Pro Gln Ile Cys Met Leu
            260                 265                 270

Lys Thr His Val Asp Ile Leu Ser Asp Phe Thr Pro Asp Phe Gly Ser
        275                 280                 285

Lys Leu Arg Ser Ile Ala Glu Lys His Asn Phe Leu Ile Phe Glu Asp
    290                 295                 300

Arg Lys Phe Ala Asp Ile Gly Asn Thr Val Thr Met Gln Tyr Glu Gly
305                 310                 315                 320

Gly Ile Phe Arg Ile Leu Asp Trp Ala Asp Ile Val Asn Ala His Ile
                325                 330                 335

Val Pro Gly Pro Gly Ile Val Asp Gly Leu Lys Leu Lys Gly Leu Pro
            340                 345                 350

Lys Gly Arg Gly Leu Leu Leu Ala Glu Met Ser Ser Ala Gly Asn
        355                 360                 365

Leu Ala His Gly Asp Tyr Thr Ala Ala Val Lys Ile Ala Glu Gln
    370                 375                 380

His Ser Asp Phe Val Met Gly Phe Ile Ser Val Asn Pro Glu Ser Trp
```

```
                385                 390                 395                 400
            Ser Val Lys Pro Ser Ser Pro Ala Phe Ile His Ala Thr Pro Gly Val
                            405                 410                 415

Gln Met Val Ala Gly Gly Asp Asp Leu Gly Gln Gln Tyr Asn Thr Pro
                        420                 425                 430

Glu Ser Val Ile Asn Tyr Arg Gly Ser Asp Ile Ile Val Gly Arg
                    435                 440                 445

Gly Ile Ile Lys Ala Ser Asp Pro Met Lys Lys Ala Trp Glu Tyr Arg
                450                 455                 460

Leu Gln Gly Trp Gln Ala Tyr Lys Asn Ser Leu Leu
            465                 470                 475

<210> SEQ ID NO 9
<211> LENGTH: 1889
<212> TYPE: DNA
<213> ORGANISM: Zea mays

<400> SEQUENCE: 9
ccacgcgtcc gtacaaagcc acttcctgct ctcgctccgc cgccgccgcc tccctcccca      60
gtcgatcacc aaacctcagt ccaaactcca aaccccgcc gcatcagaaa aaaccctag     120
gccatggacg ccgcggcgct ggagtcgctc atcctggacc tccacgccat cgaggtcgtg    180
aagctgggct ccttcacgct caagtccggc atcaaatcgc ccatctacct cgacctccgc    240
gcgctcgtct cccaccgcg cctgctctcc gccgtcgcct cgctccttca cgcgctcccg     300
gccacgcgcc cctacggcct cgtctgcggt gtcccctaca ccgcgctccc catcgccgcc    360
gtcctctccg tcgaccgctc aatccccatg ctcatgcgcc gcaaggaggt caaggcccac    420
ggcaccgcca agtccatcga gggctccttc agccccgggg acaccgtcct catcatcgag    480
gacctcgtca ccagtggcgc ctccgtgctc gagaccgccg cccgctccg cgccgagggg    540
ctcgtcgtcg ccgacgccgt agtcgtcgtc gaccgcgagc agggtggcag ggagaacctc    600
gccgctaatg ggatcacgct gcactcgctc atgacccctca cggaggtgct ggccgtgctg    660
ctcaagcacg ggaaggtgac cgaggagaag gcgcaggagg tgaggcagtt cctcgacgcc    720
aacaggaagg tggcggtgcc tggggcagca cctgttacac ccagggtgct cagaaagaca    780
ttttcggaga gggcgaatct tgccaccaac cctatgggga agaagctctt cgagctgatg    840
gagaccaagc agaccaacct gtgtgttgcc gctgatgtcg ggacaacaaa ggaactcctt    900
gagctggctg acaaggtcgg ccctcaaatt tgtatgttga aaacccatgt ggatatatta    960
tctgatttta ccccagattt tggctctaag ctccgctcga ttgctgagaa gcacaacttt   1020
ttgatcttcg aagaccgcaa gtttgctgac attggaaata cagtaaccat gcaatatgaa   1080
ggaggaatat tccgcatatt ggattgggcc gatattgtta atgcgcatat agtacctgga   1140
cctggaatcg tagatggctt gaagctgaag ggtttgccta aggaagagg ctacttctg    1200
ctcgctgaga tgagctctgc cggcaacctt gcccatggag attacactgc tgctgccgta   1260
aagattgctg agcaacattc tgattttgtg atgggattta tatcagtaaa tcctgagtct   1320
tggtcagtaa aaccatcaag ccctgcattt atccatgcca cgcctggagt tcagatggtc   1380
gcaggaggag atgatcttgg caacaatac aacactcccg aatctgtgat aaactacagg   1440
ggcagtgaca taatcatagt tggccgtggg attataaagg cgagcgatcc tatgaagaag   1500
gcgtgggagt accgcttgca aggtggcag gcatacaaga acagcttgct atgaaggaag   1560
gggggcgcca tgagcatccc caagtataag ggcgaatcca gtcagtttgg cgaaataagc   1620
```

-continued

```
gcatgcggaa aggttttcct gcagttgagt caggacctaa ttgacatcag attcactgca    1680
gaggagactc atgccccatc atcgtttctg ttacaataat ttcctctcgg tttaccctgt    1740
tcttgctggt tgagttaggc acgttgtgat gcctgtgcgc ggttaaatcg tcttactgcc    1800
atgccacttg aggtttggac tcttgagcaa gcaattttat cgatgccgag aattgtatga    1860
aaaaaaaaaa aaaaaaaaaa aaaaaaaag                                      1889
```

<210> SEQ ID NO 10
<211> LENGTH: 476
<212> TYPE: PRT
<213> ORGANISM: Zea mays

<400> SEQUENCE: 10

```
Met Asp Ala Ala Ala Leu Glu Ser Leu Ile Leu Asp Leu His Ala Ile
 1               5                  10                  15

Glu Val Val Lys Leu Gly Ser Phe Thr Leu Lys Ser Gly Ile Lys Ser
            20                  25                  30

Pro Ile Tyr Leu Asp Leu Arg Ala Leu Val Ser His Pro Arg Leu Leu
        35                  40                  45

Ser Ala Val Ala Ser Leu Leu His Ala Leu Pro Ala Thr Arg Pro Tyr
    50                  55                  60

Gly Leu Val Cys Gly Val Pro Tyr Thr Ala Leu Pro Ile Ala Ala Val
65                  70                  75                  80

Leu Ser Val Asp Arg Ser Ile Pro Met Leu Met Arg Arg Lys Glu Val
                85                  90                  95

Lys Ala His Gly Thr Ala Lys Ser Ile Glu Gly Ser Phe Ser Pro Gly
            100                 105                 110

Asp Thr Val Leu Ile Ile Glu Asp Leu Val Thr Ser Gly Ala Ser Val
        115                 120                 125

Leu Glu Thr Ala Ala Pro Leu Arg Ala Glu Gly Leu Val Val Ala Asp
    130                 135                 140

Ala Val Val Val Asp Arg Glu Gln Gly Gly Arg Glu Asn Leu Ala
145                 150                 155                 160

Ala Asn Gly Ile Thr Leu His Ser Leu Met Thr Leu Thr Glu Val Leu
                165                 170                 175

Ala Val Leu Leu Lys His Gly Lys Val Thr Glu Lys Ala Gln Glu
            180                 185                 190

Val Arg Gln Phe Leu Asp Ala Asn Arg Lys Val Ala Val Pro Gly Ala
        195                 200                 205

Ala Pro Val Thr Pro Arg Val Leu Arg Lys Thr Phe Ser Glu Arg Ala
    210                 215                 220

Asn Leu Ala Thr Asn Pro Met Gly Lys Lys Leu Phe Glu Leu Met Glu
225                 230                 235                 240

Thr Lys Gln Thr Asn Leu Cys Val Ala Ala Asp Val Gly Thr Thr Lys
                245                 250                 255

Glu Leu Leu Glu Leu Ala Asp Lys Val Gly Pro Gln Ile Cys Met Leu
            260                 265                 270

Lys Thr His Val Asp Ile Leu Ser Asp Phe Thr Pro Asp Phe Gly Ser
        275                 280                 285

Lys Leu Arg Ser Ile Ala Glu Lys His Asn Phe Leu Ile Phe Glu Asp
    290                 295                 300

Arg Lys Phe Ala Asp Ile Gly Asn Thr Val Thr Met Gln Tyr Glu Gly
305                 310                 315                 320

Gly Ile Phe Arg Ile Leu Asp Trp Ala Asp Ile Val Asn Ala His Ile
```

```
                    325                 330                 335
Val Pro Gly Pro Gly Ile Val Asp Gly Leu Lys Leu Lys Gly Leu Pro
            340                 345                 350
Lys Gly Arg Gly Leu Leu Leu Ala Glu Met Ser Ser Ala Gly Asn
        355                 360                 365
Leu Ala His Gly Asp Tyr Thr Ala Ala Val Lys Ile Ala Glu Gln
370                 375                 380
His Ser Asp Phe Val Met Gly Phe Ile Ser Val Asn Pro Glu Ser Trp
385                 390                 395                 400
Ser Val Lys Pro Ser Pro Ala Phe Ile His Ala Thr Pro Gly Val
            405                 410                 415
Gln Met Val Ala Gly Gly Asp Leu Gly Gln Gln Tyr Asn Thr Pro
            420                 425                 430
Glu Ser Val Ile Asn Tyr Arg Gly Ser Asp Ile Ile Ile Val Gly Arg
            435                 440                 445
Gly Ile Ile Lys Ala Ser Asp Pro Met Lys Lys Ala Trp Glu Tyr Arg
    450                 455                 460
Leu Gln Gly Trp Gln Ala Tyr Lys Asn Ser Leu Leu
465                 470                 475
```

```
<210> SEQ ID NO 11
<211> LENGTH: 1627
<212> TYPE: DNA
<213> ORGANISM: Oryza sativa
<220> FEATURE:
<221> NAME/KEY: unsure
<222> LOCATION: (1489)
<223> OTHER INFORMATION: n = A, C, G or T
<220> FEATURE:
<221> NAME/KEY: unsure
<222> LOCATION: (1497)
<223> OTHER INFORMATION: n = A, C, G or T
<220> FEATURE:
<221> NAME/KEY: unsure
<222> LOCATION: (1520)
<223> OTHER INFORMATION: n = A, C, G or T
<220> FEATURE:
<221> NAME/KEY: unsure
<222> LOCATION: (1558)
<223> OTHER INFORMATION: n = A, C, G or T
<220> FEATURE:
<221> NAME/KEY: unsure
<222> LOCATION: (1565)..(1566)
<223> OTHER INFORMATION: n = A, C, G or T
<220> FEATURE:
<221> NAME/KEY: unsure
<222> LOCATION: (1585)
<223> OTHER INFORMATION: n = A, C, G or T
<220> FEATURE:
<221> NAME/KEY: unsure
<222> LOCATION: (1587)
<223> OTHER INFORMATION: n = A, C, G or T
<220> FEATURE:
<221> NAME/KEY: unsure
<222> LOCATION: (1599)
<223> OTHER INFORMATION: n = A, C, G or T
<220> FEATURE:
<221> NAME/KEY: unsure
<222> LOCATION: (1612)
<223> OTHER INFORMATION: n = A, C, G or T
<220> FEATURE:
<221> NAME/KEY: unsure
<222> LOCATION: (1622)
<223> OTHER INFORMATION: n = A, C, G or T

<400> SEQUENCE: 11
gcacgagctt acacccgccc aaaaccctag ctaagcctag ccgccatgga cgccgccgcg    60
```

-continued

```
caggaatccc tcatcctgga gctccacgcc atcgaggcca tcaagttcgg caccttcgtg    120
ctcaagtccg gcatcacctc cccgatctac ctcgacctcc gcgcgctcgt ctcccacccg    180
ggcctcctct cctccatcgc caccctcctc cacaccctcc cggcgacccg ccctacgac    240 ctcctctgcg gcgtccccta caccgcgctc ccatcgcct ccgtcctctc cgtccaccgc    300
tccgtcccca tggtcatgcg ccgcaaggag gccaaggccc acggcaccgc caagtccatc    360
gagggcgcct ccgcgccgg ggaggccgtg ctcatcatcg aggacctcgt caccagcggc    420
gcctccgttc tcgagaccgc cgcgccgctc cgcgaccagg ggctcgtcgt cgccgacgcc    480
gtcgtcgtcg tcgaccgcaa gcagggcggg agggagaacc ttgccgccaa tgggatcacg    540
ctgcactcgc tcatgaccct cacggaggtg ctcgccgtgc tgctcaagca cgggaaggtg    600
acccaagaag agcgaggagg taagcagttt cttgacgcca ataggaaggt gaccgttccc    660
ggagcggcgg cgccgttaa gcccaaagcg gtcaggaagg ggtttgctga gagggctgga    720
ttggccaaga acccgatggg gaagaggctt ttcgaggtga tggaggcaaa gcagagcaat    780
ttatgtgttg ctgccgatgt gggaactgca aaggagctcc ttgagcttgc agagaaggtt    840
ggtccagaga tttgcatgct gaaaactcat gtggatatct tgtctgactt tactccagat    900
tttgagctca agcttcgctc gattgccgag aagcacaact tttgatatt tgaagaccgc    960 aagtttgctg acattggaaa cacagtgact atgcaatatg aaggaggaat atttcgcata   1020
ttagactggg ctgatatcgt caatgcccat ataattcctg gacctggaat tgtggatggt   1080
ctgaagctta agggtttgcc aaaaggaaga gggctgcttt tgcttgctga atgagctcg   1140 gctggcaacc ttgctcatgg agagtacact gctgcagctg taaagattgc tgagcaacat   1200
tctgattttg taattggatt tatatccgtt aatccagcat cttggtcagt tgcgccatca   1260
agtccagcat ttatccatgc cactcctgga gtgcagatgg tttctggagg agatgctctt   1320
ggtcaacagt acaataccc tcattctgtt ataaacgaca gaggcaagt gacataatta   1380 tagtccggac gagggattat aaaggcgaag taatccagcc cgagaccgcg agggaagtac   1440
cgcatccaag ggtgggggag caaaacaatc cagctttgcc atgagaaant gagaatngtg   1500
tttaggcaat ggttggttcn agcttatgat ttattataac caagaataat taagccanga   1560
ttgcnnataa agccgggatt aatantnaag ctgccatana aataaactgt gnagttggtt   1620 gntttgg                                                             1627
```

<210> SEQ ID NO 12
<211> LENGTH: 443
<212> TYPE: PRT
<213> ORGANISM: Oryza sativa

<400> SEQUENCE: 12

```
Met Asp Ala Ala Ala Gln Glu Ser Leu Ile Leu Glu Leu His Ala Ile
  1               5                  10                  15

Glu Ala Ile Lys Phe Gly Thr Phe Val Leu Lys Ser Gly Ile Thr Ser
                 20                  25                  30

Pro Ile Tyr Leu Asp Leu Arg Ala Leu Val Ser His Pro Gly Leu Leu
             35                  40                  45

Ser Ser Ile Ala Thr Leu Leu His Thr Leu Pro Ala Thr Arg Pro Tyr
         50                  55                  60

Asp Leu Leu Cys Gly Val Pro Tyr Thr Ala Leu Pro Ile Ala Ser Val
     65                  70                  75                  80

Leu Ser Val His Arg Ser Val Pro Met Val Met Arg Arg Lys Glu Ala
                 85                  90                  95
```

-continued

```
Lys Ala His Gly Thr Ala Lys Ser Ile Glu Gly Ala Phe Arg Ala Gly
            100                 105                 110
Glu Ala Val Leu Ile Ile Glu Asp Leu Val Thr Ser Gly Ala Ser Val
        115                 120                 125
Leu Glu Thr Ala Ala Pro Leu Arg Asp Gln Gly Leu Val Ala Asp
    130                 135                 140
Ala Val Val Val Val Asp Arg Lys Gln Gly Arg Glu Asn Leu Ala
145                 150                 155                 160
Ala Asn Gly Ile Thr Leu His Ser Leu Met Thr Leu Thr Glu Val Leu
                165                 170                 175
Ala Val Leu Leu Lys His Gly Lys Val Thr Gln Glu Glu Arg Gly Gly
            180                 185                 190
Lys Gln Phe Leu Asp Ala Asn Arg Lys Val Thr Val Pro Gly Ala Ala
        195                 200                 205
Gly Ala Val Lys Pro Lys Ala Val Arg Lys Gly Phe Ala Glu Arg Ala
    210                 215                 220
Gly Leu Ala Lys Asn Pro Met Gly Lys Arg Leu Phe Glu Val Met Glu
225                 230                 235                 240
Ala Lys Gln Ser Asn Leu Cys Val Ala Ala Asp Val Gly Thr Ala Lys
                245                 250                 255
Glu Leu Leu Glu Leu Ala Glu Lys Val Gly Pro Glu Ile Cys Met Leu
            260                 265                 270
Lys Thr His Val Asp Ile Leu Ser Asp Phe Thr Pro Asp Phe Gly Ala
        275                 280                 285
Lys Leu Arg Ser Ile Ala Glu Lys His Asn Phe Leu Ile Phe Glu Asp
    290                 295                 300
Arg Lys Phe Ala Asp Ile Gly Asn Thr Val Thr Met Gln Tyr Glu Gly
305                 310                 315                 320
Gly Ile Phe Arg Ile Leu Asp Trp Ala Asp Ile Val Asn Ala His Ile
                325                 330                 335
Ile Pro Gly Pro Gly Ile Val Asp Gly Leu Lys Leu Lys Gly Leu Pro
            340                 345                 350
Lys Gly Arg Gly Leu Leu Leu Ala Glu Met Ser Ser Ala Gly Asn
        355                 360                 365
Leu Ala His Gly Glu Tyr Thr Ala Ala Ala Val Lys Ile Ala Glu Gln
    370                 375                 380
His Ser Asp Phe Val Ile Gly Phe Ile Ser Val Asn Pro Ala Ser Trp
385                 390                 395                 400
Ser Val Ala Pro Ser Ser Pro Ala Phe Ile His Ala Thr Pro Gly Val
                405                 410                 415
Gln Met Val Ser Gly Gly Asp Ala Leu Gly Gln Gln Tyr Asn Thr Pro
            420                 425                 430
His Ser Val Ile Asn Asp Lys Arg Gln Val Thr
        435                 440

<210> SEQ ID NO 13
<211> LENGTH: 476
<212> TYPE: PRT
<213> ORGANISM: Arabidopsis thaliana

<400> SEQUENCE: 13

Met Ser Ala Met Glu Ala Leu Ile Leu Gln Leu His Glu Ile Gly Ala
  1               5                  10                  15
Val Lys Phe Gly Asn Phe Lys Leu Lys Ser Gly Ile Phe Ser Pro Val
```

-continued

```
             20                  25                  30
Tyr Ile Asp Leu Arg Leu Ile Val Ser Tyr Pro Ser Leu Leu Thr Gln
             35                  40                  45
Ile Ser Gln Thr Leu Ile Ser Ser Leu Pro Pro Ser Ala Thr Phe Asp
 50                  55                  60
Val Val Cys Gly Val Pro Tyr Thr Ala Leu Pro Ile Ala Thr Val Val
 65                  70                  75                  80
Ser Val Ser Asn Gly Ile Pro Met Leu Met Arg Arg Lys Glu Ile Lys
                 85                  90                  95
Asp Tyr Gly Thr Ser Lys Ala Ile Glu Gly Ile Phe Glu Lys Asp Gln
                100                 105                 110
Thr Cys Leu Ile Ile Glu Asp Leu Val Thr Ser Gly Ala Ser Val Leu
                115                 120                 125
Glu Thr Ala Ala Pro Leu Arg Ala Val Gly Leu Lys Val Ser Asp Ala
130                 135                 140
Val Val Leu Ile Asp Arg Gln Gln Gly Gly Arg Glu Asn Leu Ala Glu
145                 150                 155                 160
Asn Gly Ile Lys Leu His Ser Met Ile Met Leu Thr Asp Met Val Arg
                165                 170                 175
Val Leu Lys Glu Lys Gly Lys Ile Glu Glu Val Glu Val Asn Leu
                180                 185                 190
Leu Lys Phe Leu Glu Glu Asn Arg Arg Val Ser Val Pro Ser Val Glu
            195                 200                 205
Lys Pro Lys Pro Lys Pro Arg Val Leu Gly Phe Lys Glu Arg Ser Glu
        210                 215                 220
Leu Ser Lys Asn Pro Thr Gly Lys Lys Leu Phe Asp Ile Met Leu Lys
225                 230                 235                 240
Lys Glu Thr Asn Leu Cys Leu Ala Ala Asp Val Gly Thr Ala Ala Glu
                245                 250                 255
Leu Leu Asp Ile Ala Asp Lys Val Gly Pro Glu Ile Cys Leu Leu Lys
                260                 265                 270
Thr His Val Asp Ile Leu Pro Asp Phe Thr Pro Asp Phe Gly Ser Lys
            275                 280                 285
Leu Arg Ala Ile Ala Asp Lys His Lys Phe Leu Ile Phe Glu Asp Arg
    290                 295                 300
Lys Phe Ala Asp Ile Gly Asn Thr Val Thr Met Gln Tyr Glu Gly Gly
305                 310                 315                 320
Ile Phe Lys Ile Leu Glu Trp Ala Asp Ile Ile Asn Ala His Val Ile
                325                 330                 335
Ser Gly Pro Gly Ile Val Asp Gly Leu Lys Leu Lys Gly Met Pro Arg
            340                 345                 350
Gly Arg Gly Leu Leu Leu Leu Ala Glu Met Ser Ser Ala Gly Asn Leu
        355                 360                 365
Ala Thr Gly Asp Tyr Thr Ala Ala Val Lys Ile Ala Asp Ala His
370                 375                 380
Ser Asp Phe Val Met Gly Phe Ile Ser Val Asn Pro Ala Ser Trp Lys
385                 390                 395                 400
Cys Gly Tyr Val Tyr Pro Ser Met Ile His Ala Thr Pro Gly Val Gln
                405                 410                 415
Met Val Lys Gly Gly Asp Ala Leu Gly Gln Gln Tyr Asn Thr Pro His
                420                 425                 430
Ser Val Ile Thr Glu Arg Gly Ser Asp Ile Ile Ile Val Gly Arg Gly
            435                 440                 445
```

```
Ile Ile Lys Ala Glu Asn Pro Ala Glu Thr Ala His Glu Tyr Arg Val
        450                 455                 460

Gln Gly Trp Asn Ala Tyr Leu Glu Lys Cys Ser Gln
465                 470                 475

<210> SEQ ID NO 14
<211> LENGTH: 476
<212> TYPE: PRT
<213> ORGANISM: Nicotiana tabacum

<400> SEQUENCE: 14

Met Ser Ala Met Glu Ala Leu Ile Leu Gln Leu His Glu Ile Gly Ala
  1               5                  10                  15

Val Lys Phe Gly Asn Phe Lys Leu Lys Ser Gly Ile Phe Ser Pro Val
                 20                  25                  30

Tyr Ile Asp Leu Arg Leu Ile Val Ser Tyr Pro Ser Leu Leu Thr Gln
             35                  40                  45

Ile Ser Gln Thr Leu Ile Ser Ser Leu Pro Pro Ser Ala Thr Phe Asp
         50                  55                  60

Val Val Cys Gly Val Pro Tyr Thr Ala Leu Pro Ile Ala Thr Val Val
 65                  70                  75                  80

Ser Val Ser Asn Gly Ile Pro Met Leu Met Arg Arg Lys Glu Ile Lys
                 85                  90                  95

Asp Tyr Gly Thr Ser Lys Ala Ile Glu Gly Ile Phe Glu Lys Asp Gln
            100                 105                 110

Thr Cys Leu Ile Ile Glu Asp Leu Val Thr Ser Gly Ala Ser Val Leu
        115                 120                 125

Glu Thr Ala Ala Pro Leu Arg Ala Val Gly Leu Lys Val Ser Asp Ala
    130                 135                 140

Val Val Leu Ile Asp Arg Gln Gln Gly Gly Arg Glu Asn Leu Ala Glu
145                 150                 155                 160

Asn Gly Ile Lys Leu His Ser Met Ile Met Leu Thr Asp Met Val Arg
                165                 170                 175

Val Leu Lys Glu Lys Gly Lys Ile Glu Glu Glu Val Glu Val Asn Leu
            180                 185                 190

Leu Lys Phe Leu Glu Glu Asn Arg Arg Val Ser Val Pro Ser Val Glu
        195                 200                 205

Lys Pro Lys Pro Lys Pro Arg Val Leu Gly Phe Lys Glu Arg Ser Glu
    210                 215                 220

Leu Ser Lys Asn Pro Thr Gly Lys Lys Leu Phe Asp Ile Met Leu Lys
225                 230                 235                 240

Lys Glu Thr Asn Leu Cys Leu Ala Ala Asp Val Gly Thr Ala Ala Glu
                245                 250                 255

Leu Leu Asp Ile Ala Asp Lys Val Gly Pro Glu Ile Cys Leu Leu Lys
            260                 265                 270

Thr His Val Asp Ile Leu Pro Asp Phe Thr Pro Asp Phe Gly Ser Lys
        275                 280                 285

Leu Arg Ala Ile Ala Asp Lys His Lys Phe Leu Ile Phe Glu Asp Arg
    290                 295                 300

Lys Phe Ala Asp Ile Gly Asn Thr Val Thr Met Gln Tyr Glu Gly Gly
305                 310                 315                 320

Ile Phe Lys Ile Leu Glu Trp Ala Asp Ile Ile Asn Ala His Val Ile
                325                 330                 335

Ser Gly Pro Gly Ile Val Asp Gly Leu Lys Leu Lys Gly Met Pro Arg
```

-continued

```
                              340                          345                          350
        Gly Arg Gly Leu Leu Leu Ala Glu Met Ser Ser Ala Gly Asn Leu
                355                          360                  365

Ala Thr Gly Asp Tyr Thr Ala Ala Val Lys Ile Ala Asp Ala His
                370                          375              380

Ser Asp Phe Val Met Gly Phe Ile Ser Val Asn Pro Ala Ser Trp Lys
        385                      390                      395                  400

Cys Gly Tyr Val Tyr Pro Ser Met Ile His Ala Thr Pro Gly Val Gln
                        405                      410              415

Met Val Lys Gly Gly Asp Ala Leu Gly Gln Gln Tyr Asn Thr Pro His
                        420                  425                  430

Ser Val Ile Thr Glu Arg Gly Ser Asp Ile Ile Val Gly Arg Gly
                    435                  440                  445

Ile Ile Lys Ala Glu Asn Pro Ala Glu Thr Ala His Glu Tyr Arg Val
                450                  455                  460

Gln Gly Trp Asn Ala Tyr Leu Glu Lys Cys Ser Gln
        465                  470                  475
```